United States Patent [19]

Izawa et al.

[11] 4,035,417

[45] July 12, 1977

[54] PROCESS FOR PRODUCING ACRYLIC ACID OR METHACRYLIC ACID

[75] Inventors: Shoichi Izawa; Isao Ono; Tetuo Iikuni; Kiyoto Nishida, all of Yamaguchi, Japan

[73] Assignee: Rohm and Haas Company, Philadelphia, Pa.

[21] Appl. No.: 522,251

[22] Filed: Nov. 6, 1974

Related U.S. Application Data

[60] Division of Ser. No. 381,335, July 20, 1973, Pat. No. 3,959,182, which is a continuation-in-part of Ser. No. 851,429, Aug. 19, 1969, abandoned.

[30] Foreign Application Priority Data

Mar. 30, 1966  Japan .............................. 41-19772

[51] Int. Cl.$^2$ ........................................ C07C 51/32
[52] U.S. Cl. ........................... 260/530 N; 252/435; 252/437; 252/464; 252/467
[58] Field of Search ................... 260/533 N, 530 N; 252/435, 437, 464, 467

[56] References Cited

U.S. PATENT DOCUMENTS

| | | | |
|---|---|---|---|
| 3,238,253 | 3/1966 | Kerr | 260/530 N |
| 3,352,905 | 11/1967 | Kerr | 260/530 N |
| 3,530,175 | 9/1970 | Yanagita | 260/530 N |
| 3,711,540 | 1/1973 | Nonnenmacher | 260/530 N |
| 3,773,828 | 11/1973 | Kadowaki | 260/530 N |

FOREIGN PATENT DOCUMENTS

| | | | |
|---|---|---|---|
| 416,262 | 4/1966 | Japan | 260/530 N |
| 1,154,148 | 6/1969 | United Kingdom | 260/533 N |

*Primary Examiner*—Vivian Garner
*Attorney, Agent, or Firm*—Wenderoth, Lind & Ponack

[57] ABSTRACT

An improvement in the process for producing acrylic or methacrylic acid by the vapor phase catalytic oxidation of a system containing acrolein or methacrolein, respectively, is provided. The improvement resides in the employment, in such process, of a novel catalyst prepared by admixing with a solution of the catalytic component an organic substance, for example from the group of organic acids, alcohols, amines and esters, drying the admixture and subsequently calcining the admixture at a temperature in the range of 330° C to 430° C to form the novel catalyst.

18 Claims, No Drawings

PROCESS FOR PRODUCING ACRYLIC ACID OR METHACRYLIC ACID

This application is a divisional application of Ser. No. 381,335, filed July 20, 1973, now U.S. Pat. at No. 3,959,182, which in turn is a continuation-in-part application of Ser. No. 851,429, filed Aug. 19, 1969, now abandoned which in turn is a substitute application of Ser. No. 626,971, filed Mar. 30, 1967, now abandoned.

The present invention relates to a process for producing acrylic acid or methacrylic acid by the catalytic vapor phase oxidation of acrolein or methacrolein, respectively, or of a composition containing acrolein or methacrolein obtained by means of the vapor phase catalytic oxidation of propylene or isobutylene. More particularly, it relates to the improvement wherein a novel oxidation catalyst as defined herein is employed in the oxidation process. The invention also provides the novel catalyst as well as the process for preparing such catalyst.

A catalyst which consists of molybdenum oxide and vanadium oxide and which has superior efficiency in the process wherein acrylic acid is produced by means of the vapor phase oxidation of acrolein is known. See Japanese patent publication Sho 41-1775. This publication suggests a molybdenum to vanadium ratio, calculated as $MoO_3$ to $V_2O_5$ of 2:1 to 8:1. Further research with respect to such catalysts has resulted in the discovery of related but novel catalysts which are particularly effective in the process.

The present invention provides a means of further elevating the catalytic activity of such types of catalysts. In the instant process an organic substance is added to an aqueous solution containing the components of the catalyst and the resultant solution is evaporated to dryness. The dry composition is then continuously calcined at a temperature in the range of 330° to 430° C as air is blown through the mixture.

The novel catalyst prepared in this manner has a remarkable catalytic effect in the formation of acrylic acid or methacrylic acid by means of air oxidation of acrolein air methacrolein and this fact is experimentally demonstrated. The catalytic vapor phase oxidation of acrolein or methacrolein or a composition containing such materials to produce, respectively, acrylic or methacrylic acid is, per se, known, as are the essential reaction conditions. The present invention provides an improvement wherein the novel catalyst produced in accordance with the instant disclosure is employed.

Heretofore, a process of adding an alkanolamine, such as ethanolamine, or an organic acid, such as oxalic acid, has been known in preparing an oxidation catalyst. See, for example, *Chemistry*, special number, Vol. 2, *Catalyst Chemistry*, page 204, (1957), and British Pat. No. 903,034. However, according to the process of the present invention, the catalyst prepared by addition of an organic substance demonstrates the phenomenon of promoting remarkably the efficiency of the catalytic process when the temperature of calcining the said catalyst composition during its preparation is appropriately selected. The criticality of the temperature range employed in preparing the catalyst has not previously been described. The present invention is based on the discovery of the critical fact that the effect of addition of organic substance is remarkably affected by the calcining temperature employed in the preparation of the catalyst composition.

The nature of the present invention is further explained in detail below.

The principal components employed in the catalyst compositions of this invention are molybdenum oxides and vanadium oxides. They are preferably employed in the composition at a weight ratio of molybdenum oxide to vanadium oxide within the range of 2:1 to 8:1.

As starting materials in the preparation of the catalyst compositions water-soluble salts of molybdenum and vanadium as for example, ammonium molybdate and ammonium metavanadate respectively may be employed. Also chloride, sulfate, nitrate, etc. of molybdenum, and vanadium can be transformed into an oxide by calcining them and then dissolving the oxide in an aqueous ammonia solution. Therefore, it is, of course, possible that the oxides of molybdenum and vanadium are transformed into an ammonium salt. Such materials may be employed as the principal constituents of the catalyst composition alone or in conjunction with additional known additives or modifiers, as, for example, phosphoric acid.

To a solution of the primary constituents of the catalyst composition, as, for example, an aqueous solution of such materials, the organic substance utilized as an additive is added and intimately admixed. These organic substances useful in conjunction with this invention comprise essentially (a) carboxylic acids and acid anhydrides including amino acids as well as oxy acids for example, oxalic acid, tartaric acid, sebacic acid, adipic acid, benzoic acid, salicylic acid, citric acid, succinic acid, lactic acid, fumaric acid, dl-malic acid, ethylenediamine tetraacetic acid, phthalic anhydride, β-alanine, (b) alcohols, including amino alcohols, for example, pentaerythritol, methoxy butanol, ethylene glycol, diethylene glycol, 1,3-butylene glycol, propylene glycol, polyethylene glycol, polypropylene glycol, glycerol, diacetone alcohol, lauryl alcohol, hydroquinone (c) amides and lactams for example, Uretoropin, monoethanol amine, diethanol amine, triethanol amine, hexamethylene diamine, caprolactam, acetoanilide, diphenyl amine, α-naphthyl amine, m-phenylene diamine, methyl aniline, diethylene triamine, triethylene tetramine, (d) esters, ethers, ketones, for example, ethyl acetoacetate, methyl acetoacetate, itaconic ester, ethylene glycol monobutyl ether, methoxy butyl acetate, tricresyl phosphate, dioctyl phthalate, carboxy methyl cellulose (e) carbohydrates for example, gum arabic, locust bean gum, gelatine, starch, xylose, D-sorbit. All organic substances, i.e. reducing agents, having intra-molecular oxygen and/or nitrogen may be employed, such as functional derivatives of the previously mentioned compounds. As will be apparent from the subsequently presented examples, an organic substance having a boiling point of 150° C or more at standard pressure, or at the pressure utilized for calcination of the mixture, and at least some degree of solubility in water is, however, not the most essential condition of the organic substance. This will be evident by consideration of the fact that the gums, carbohydrates, gelatin, and the like mentioned above may not be strictly water soluble but they nevertheless are such that they will form an aquasol or aquagel in the presence of water. As organic substances falling within the above description, however, there are preferably pointed out carboxylic acids, such as oxalic acid, succinic acid, capric acid, hexanoic acid, ethylenediamine tetraacetic acid and benzoic acid, alcohols, such as lauryl alcohol, ethylene glycol, glycerol, and benzyl alcohol, and amino alcohols, such as monoethanolamine, and diethanolamine; amines, such as ethylenediamine, tetraethylene pentamine, and phenylenediamine; amino acids, such as β-alanine; oxy acids, such as lactic acid; and esters, such as dioctyl phthalate.

It is to be understood that the present invention does not reside in the use of any specific organic reducing agent, but rather in the temperature at which calcination of the mixture of molybdenum and vanadium compounds and reducing agent is carried out. Thus, as indicated above, temperatures within the range of 330°-430° C result in increased activity of the catalyst composition.

The addition of an amount of at least one of these organic substances representing at least 5%, and preferably at least 20%, and most preferably 20-60% by weight of the effective amount of oxidized metal in the catalyst, e.g. the total amount of molybdenum oxide and vanadium oxide, demonstrates remarkable effect in increasing the catalytic efficiency of the catalyst compositions.

The calcining temperature utilized in preparing the catalyst is selected in the range of 330° to 430° C and the calcination is carried out in an atmosphere containing oxygen, preferably air. The catalyst compositions prepared by calcining the admixture in the range of 370° to 400° C demonstrate particularly superior efficiency.

When a calcining temperature is selected which is below 330° C, a reaction between the added organic substance and the components of the catalyst is not satisfactorily achieved and the activity of the catalyst does not have the increased effect to the desired degree. On the other hand, when a calcining temperature is selected which is in excess of 430° C, and even if the calcination is carried out continuously, the effect of increasing the activity of the catalyst is not achieved. On the contrary, when the said resultant admixture is calcined within a temperature range of 330° to 430° C, and particularly in the range of 370° to 400° C, the activity of the catalyst is increased and additionally its high activity is exhibited for longer periods of time. This durability of the novel catalyst was manifestly shown by test lasting over a period of 3 months.

In general, the effect of the organic substance added to the oxidation catalyst components prior to calcining may be explained under the theory that the organic substance, in being oxidized during the calcination, acts to reduce the valence state or oxidation state of the metal components, thereby achieving a state of oxidation-reduction of the metals resulting ultimately in the vanadium oxide-molybdenum oxide catalyst which provides suitable active sites for the compound to be oxidized. For example, vanadium may exist in a valence state of 3 or 5. In the event pentavalent vanadium is used as in the case of ammonium meta-vanadate, it is hypothesized that during the decomposition of this compound and during the oxidation of the organic material added to the catalyst precursor, the valence state of the vanadium is modified in such a way as to perhaps modify the ultimate crystal form of the catalyst and to result in the highly selective catalyst of the invention. These and other theories and hypotheses mentioned herein are not intended to limit the invention and are merely offered as possible explanations of the phenomena observed. Whenever $MoO_3$ or $V_2O_5$ is mentioned herein, it is to be understood that the amount of oxide is calculated in that form, and that it is possible that other valence states may exist.

For regeneration of the catalyst of the present invention, the composition comprising oxides of molybdenum and vanadium may be dissolved in an ammonia aqueous solution to produce ammonium salts of molybdenum and vanadium. These salts can be prepared into the catalyst of the present invention through the present process.

According to the process of preparation of the catalyst of the present invention, the activity is remarkably affected by using a calcining temperature in the specified range and particularly in the optimum temperature range. As indicated, if the said catalyst is calcined at a temperature in excess of the desired temperature range, the increase in activity of the catalyst will be lost and the activity will be returned to that demonstrated without the addition of the organic substance. In addition to the foregoing explanation, the results of thermal analysis and X-ray diffraction measurements indicate that in employing an organic substance as an additive, if the calcination is in the specified range of temperature the substance will not be entirely decomposed and dispersed. Rather, a portion of the said organic substance will be combined with the catalytic components and thereby a crystalline composition will be achieved which is a suitable form for particularly effective catalytic activity.

In preparing the catalyst compositions a carrier for the catalyst can be utilized. In this respect there may be mentioned granular alumina. When employing such carrier an aqueous solution of the principal catalytic component can be prepared and the organic substance added thereto. To the resultant mixture fused alumina in granular form can be added and subsequently the aqueous mixture vaporized to dryness. The catalyst composition adheres to the granular carrier. The material is then subjected to the calcination stage of the catalyst preparation.

As previously indicated, the catalytic vapor phase oxidation of acrolein or methacrolein is known, as are the reaction conditions employed in such vapor phase catalytic oxidation. In connection with the present invention, the conventional procedures can be employed substituting the novel catalyst of the present invention for the previously employed catalyst.

The following examples are set forth to illustrate the present invention. Such examples are purely illustrative and are not to be taken as exhaustive of the invention.

EXAMPLE I 21.6g of ammonium molybdate [$(NH_4)_6Mo_7O_{24} \cdot 4H_2O$] and 5.66g of ammonium meta-vanadate [$NH_4VO_3$] were heated to dissolution in 150cc of water. 6.6g of glycerol were added to the resultant mixture and after stirring, 100g of fused alumina in granular shape (4m/m in diameter), as a carrier, were added to the said resultant mixture. As the mixture was agitated occasionally and vaporized, the catalyst composition was adhered to the granular carrier. After the mixture was evaporated to dryness, it was further dried at a temperature of 100° to 130° C for 2 hours and put into a quartz U-shaped tube.

Air was blown into one end of the said tube, the said tube was immersed in a bath of molten salt at 350° C and the mixture was calcined for two hours. This mixture was calcined for four hours by elevating the temperatures of the molten salt to 380° C. The mixture was then removed from the tube.

22.5g of the catalyst (containing 4.0g of $MoO_3$ + $V_2O_5$) were placed in a 16m/m inside diameter quartz U-shaped tube and the said tube was immersed in the bath of molten salt at 270° C. A mixed gas, having a composition of 5.0 molar percent of acrolein, 32.5 molar percent of air and 62.5 molar percent of steam was fed into the said tube at a velocity of 1 mol/hr and the gas was allowed to react in the presence of the said catalyst. The temperature of the bath of molten salt was adjusted so that the maximum temperature of the catalyst bed was maintained at 300° C. The results obtained in this procedure were 92% conversion for acrolein and 91% selectivity for acrylic acid.

EXAMPLE II

The amounts of glycerol used in the process of Example I were varied and the reactions were carried out under the same conditions as that in Example I.

The results are set forth below:

| Addition amount of glycerol | | Conversion of acrolein | Selectivity of acrylic acid |
| --- | --- | --- | --- |
| 0 | g* | 22.8 % | 88.5 % |
| 1.1 | ( 5.0) | 37.6 | 92.4 |
| 2.2 | (10.0) | 54.7 | 90.7 |
| 4.4 | (20.0) | 88.4 | 91.0 |
| 8.8 | (40.0) | 92.0 | 91.2 |
| 13.2 | (60.0) | 90.2 | 90.6 |

Values indicate percentage amount of glycerol in proportion to ($MoO_3$ + $V_2O_5$).

The above results demonstrate that an amount of glycerol in the range 5 – 60% in proportion to the metal oxide content of the catalyst produces substantially better results than no glycerol, and that an amount in excess of about 20% in proportion to the metal oxide content of catalyst has a remarkable efficiency.

EXAMPLE III

Various organic compounds were added in the place of glycerol in the process of Example I and the reactions were carried out under the same conditions as that in Example I.

The results are set forth below:

| Organic compound used for the addition | Conversion of acrolein | Selectivity of acrylic acid |
| --- | --- | --- |
| Oxalic acid | 67.4 % | 87.6 |
| Succinic acid | 82.5 | 90.2 |
| Lactic acid | 74.2 | 89.8 |
| Ethanol amine | 54.7 | 89.4 |
| Diethanol amine | 93.8 | 89.2 |
| Ethylene glycol | 65.3 | 87.4 |
| Diethylene glycol | 92.7 | 89.4 |
| Propylene glycol | 71.3 | 90.2 |
| Diethylene triamine | 85.4 | 91.4 |
| Triethylene tetramine | 96.2 | 87.9 |
| Lauryl alcohol | 48.4 | 87.5 |
| Dioctyl phthalate | 57.5 | 87.6 |
| Tricresyl phosphate | 47.5 | 89.4 |
| Hydroquinone | 73.6 | 86.3 |
| β-alanine | 67.4 | 85.4 |

From the above Table it is seen that when use is made of an organic substance as an additive, which additive has a high boiling point for water, such can be expected to have the effect of raising the catalyst efficiency.

EXAMPLE IV

The calcining temperature employed in preparing the catalyst by the process of Example I was varied and the results are shown in the following Table.

| Calcining temperature* | Conversion of acrolein | Selectivity of acrylic acid |
| --- | --- | --- |
| 300° C | 25.5 % | 88.7 % |
| 330 | 43.2 | 89.2 |
| 350 | 67.4 | 90.4 |
| 370 | 84.2 | 89.2 |
| 390 | 85.0 | 90.2 |
| 400 | 72.4 | 88.4 |
| 410 | 64.2 | 87.3 |
| 430 | 47.6 | 85.6 |
| 450 | 19.9 | 80.4 |

*This temperature indicates the maximum temperature in the oxidizing zone of catalyst layer.

This Example demonstrates that the activation of catalyst is remarkably affected by the calcining temperature employed for preparing the catalyst. As set forth in the text, the calcining of the catalyst in the temperature range of 330° C to 430° C, particularly in the range of 370° C to 400° C increases remarkably the conversion of acrolein in the process wherein acrylic acid is prepared therefrom.

EXAMPLE V 21.6g ammonium molybdate [$(NH_4)_6Mo_7O_{24}\cdot 4H_2O$], 5.66g of ammonium meta-vanadate [$NH_4VO_3$], and 1.2g of phosphoric acid (85%) were heated to dissolution in 150cc of water. 4.4g of diethanolamine were added to this mixture and thereafter the resultant mixture was further admixed with 100g of granular, fused alumina, as a carrier. The mixture is vaporized and the catalyst adheres to the granular alumina carrier.

This mixture, after being evaporated to dryness was further dried at a temperature of 100° to 130° C for two hours and then put into a quartz, U-shaped tube. As the air was blown into the said tube, the said tube was immersed into a bath of molten salt at 350° C to calcine this mixture for 2 hours. The temperature was elevated to 390° C and the said mixture was further calcined for 4 hours.

A mixed gas having a composition of 5 molar percent of methacrolein, 32.5 molar percent of air and 62.5 molar percent of steam was fed at a velocity of 1.0 mol/hr into 22g of the above catalyst (containing $MoO_3$ + $V_2O_5$ + $P_2O_5$ = 4g) and the reaction was performed under the same condition similar to that in Example I.

The results recorded were respectively 87% methacrolein conversion and 75% methacrylic aid selectivity.

What is claimed is:

1. In a process for producing acrylic acid or methacrylic acid by the vapor phase catalytic air oxidation of acrolein or methacrolein, respectively, wherein the catalyst used is prepared from an admixture containing water-soluble vanadium and molybdenum compounds and an organic reducing agent having intramolecular oxygen, nitrogen or both, which organic reducing agent is at least one substance selected from the group consisting of carboxylic acids, alcohols, amines and esters and has a boiling point of 150° C or more at the pressure utilized for calcining the catalyst and is watersoluble or forms an aquasol or an aquagel in the presence of water, the improvement wherein the admixture of molybdenum compounds, vanadium compounds and reducing agent is calcined at a temperature in the range of 330° C to 430° C, and the amount of reducing agent is at least 5 percent by weight based on the combined weight of the molybdenum and vanadium oxides resulting from calcination.

2. The process according to claim 1, wherein the organic reducing agent is water-soluble and has a boiling point of at least 150° C.

3. The process according to claim 1, wherein the organic reducing agent forms an aquasol or aquagel in the presence of water and has a boiling point of at least 150° C.

4. The process according to claim 1, wherein the organic reducing agent is at least one substance selected from the group consisting of glycerol, oxalic acid, succinic acid, lactic acid, ethanol amine, diethanol amine, ethylene glycol, diethylene glycol, propylene glycol, diethylene triamine, triethylene tetramine, lauryl alcohol, dioctyl phthalate, tricresyl phosphate, hydroquinone and β-alanine.

5. The process according to claim 1, wherein the organic reducing agent is selected from the group consisting of oxalic acid, succinic acid, capric acid, hexanoic acid, ethylenediamine tetraacetic acid, benzoic acid, β-alanine and lactic acid.

6. The process according to claim 1, wherein the organic reducing agent is at least one member selected from the group consisting of lauryl alcohol, ethylene glycol, diethylene glycol, propylene glycol, glycerol and benzyl alcohol.

7. The process according to claim 1, wherein the organic reducing agent is at least one member selected from the group consisting of ethylenediamine, diethylenetriamine, triethylenetetraamine, tetraethylenepentamine, phenylenediamine, monoethanolamine and diethanolamine.

8. The process according to claim 1, wherein the organic reducing agent is selected from the group consisting of dioctyl phthalate and tricresyl phosphate.

9. The process according to claim 1, wherein the organic reducing agent is hydroquinone.

10. The process according to claim 1, wherein the water-soluble compounds are ammonium molybdate and ammonium meta-vanadate.

11. The process according to claim 10, wherein 5–60% by weight of glycerol is incorporated into an aqeuous solution of the compounds and the resultant mixture is dried and calcined.

12. The process according to claim 1, wherein acrylic acid is produced by oxidizing acrolein.

13. The process according to claim 1, wherein methacrylic acid is produced by oxidizing methacrolein.

14. The process according to claim 1, wherein the organic reducing agent is employed in an amount of at least 20% by weight of the combined weights of the molybdenum and vanadium oxides.

15. The process according to claim 1, wherein calcination is conducted at 370°–400° C.

16. The process according to claim 1, wherein fused alumina is incorporated into the admixture of the compounds.

17. The process according to claim 1, wherein phosphoric acid is incorporated into the admixture of the compounds.

18. The process according to claim 1, wherein the weight ratio of molybdenum oxide to vanadium oxide is 2:1 to 8:1.

* * * * *